United States Patent [19]

Hoffman et al.

[11] 4,140,785

[45] Feb. 20, 1979

[54] N-(BENZOTHIENOPYRAZOL)AMIDE ANTIRHINOVIRAL AGENTS

[75] Inventors: Howard E. Hoffman; Dennis R. Rayner, both of Wilmington, Del.

[73] Assignee: E. I. Du Pont de Nemours and Company, Wilmington, Del.

[21] Appl. No.: 903,877

[22] Filed: May 8, 1978

[51] Int. Cl.$^2$ .................. A61K 31/415; C07D 495/04
[52] U.S. Cl. ............................... 424/273 P; 548/359; 424/266; 260/330.5
[58] Field of Search .............................. 548/359, 370; 260/294.8 B; 424/266, 273 P

[56] References Cited

PUBLICATIONS

Awad et al., Chem. Abst. 1975, vol. 82, No. 170555v.
Chippendale et al., J. Chem. Soc., Perkin Traus. I, 1973, No. 2, pp. 129–133.

*Primary Examiner*—Natalie Trousof
*Assistant Examiner*—Natalia Harkaway

[57] ABSTRACT

Certain N-(benzothienopyrazol)amides such as 2,2-diethyl-N-(1-methyl-1-H-(1)benzothieno[3,2-c]-pyrazol-3-yl)butanamide are useful for the prophylaxis and therapy of diseases caused by rhinoviruses.

30 Claims, No Drawings

N-(BENZOTHIENOPYRAZOL)AMIDE ANTIRHINOVIRAL AGENTS

BACKGROUND OF THE INVENTION

This invention is directed to a class of novel compounds and to the use of those compounds for the treatment of diseases caused by rhinoviruses.

Unlike many other infectious agents, many viruses are intracellular parasites, the functions of which may involve the metabolic or anabolic processes of the invaded cell. For this reason, agents that inhibit or kill viruses are likely to cause injury to the host cell as well. Thus, the development of effective antiviral agents presents even more difficulty than the search for drugs to combat diseases caused by other microorganisms.

Over the course of many years, thousands of compounds have been evaluated in the search for effective agents. Very few compounds ever reach the stage of clinical testing and of these only a small number have been developed commercially. One of the best known of these agents is 1-aminoadamantane hydrochloride, which has been found to be effective for the prophylaxis and symptomatic treatment of illness caused by influenza A virus strains. Idoxuridine and adenine arabinoside are effective for the topical treatment of herpes simplex keratitis. Methisazone has been found to be effective for the prevention of smallpox; however, it is not widely used because of the virtually complete elimination of smallpox through innoculation with vaccines.

There is clearly a great need in this day and age for a compound that will be effective against rhinoviruses — the causative agents of the common cold. This need is of critical importance to the elderly and chronically ill for whom rhinovirus infections can often be dangerous. Moreover, the absenteeism and reduced ability to perform effectively, occasioned by the common cold in humans, represent an astronomical waste of resources. Thus, the need of modern society for an agent which is effective against rhinoviruses is of primary importance.

BRIEF SUMMARY OF THE INVENTION

The invention is, therefore, directed to a novel class of N-(benzothienopyrazol)amides which are intended for use in the treatment or prevention of the "common cold", an upper respiratory disease of man characterized by rhinorrhea, nasal congestion, sneezing, pharyngeal discomfort, and cough[1]. More particularly, these novel compounds are antirhinoviral agents, inhibiting the multiplication of rhinoviruses, the causative agents of the colds. In contrast to drugs used for symptomatic relief of colds, these compounds inhibit the production of the infectious agent, i.e., one or more of the over one-hundred known strains of rhinovirus. Many of these compounds are also active against certain other picornaviruses. In particular, the invention is directed to compounds corresponding to the formula

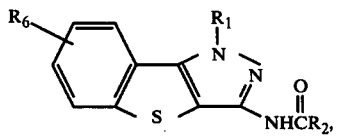

wherein
$R_1$ is methyl or ethyl;
$R_2$ is selected from cyclohexyl, phenyl, 3-pyridyl, $C_{2-5}$ haloalkyl having 1–3 halogen substituents, in other than the α-position with respect to the carbonyl group, $C_{2-5}$ alkoxyalkyl having the alkoxy moiety in other than the α-position with respect to the carbonyl group, and the group

wherein
$R_3$ and $R_4$ are independently selected from H, methyl and ethyl;
$R_5$ is selected from H and $C_{1-5}$ alkyl;
$R_6$ is H, Cl, F, methyl, 6,7-methylenedioxy, 6,7-dimethoxy, 6,7-diacetoxy or the amine group $-NR_7R_8$, wherein $R_7$ and $R_8$ are independently selected from H, methyl and ethyl;
and, when $R_2$ is 3-pyridyl and/or when $R_6$ is amine, their pharmaceutically suitable acid addition salts, such as hydrochloride or sulfate, provided that
 (a) when $R_2$ is cyclohexyl, $R_6$ is H or methyl;
 (b) when $R_2$ is phenyl, $R_6$ is H; and
 (c) when $R_2$ is 3-pyridyl, $R_6$ is H or F.

[1] Evan, A. S., Ed., Viral Infections of Humans, Plenum Publishing Co. New York, N.Y., (1976) pp. 383–408.

The invention is also directed to pharmaceutical compositions containing the above-described compounds and to the method of using them for the prophylaxis and therapy of diseases caused by rhinoviruses.

DETAILED DESCRIPTION OF THE INVENTION

Within the context of the above formula, it has been found that certain structural variations are preferred because of the indication of greater antiviral effectiveness.

In particular, it is preferred that $R_1$ be methyl and/or that $R_2$ be selected from the group consisting of 3-pyridyl, $C_{2-5}$ chloroalkyl, and a group

in which $R_3$ and $R_4$ are independently methyl or ethyl and $R_5$ is H, methyl or ethyl and/or $R_6$ is H.

Further preferred are those compounds in which more than one of the R groups is of the above-indicated preferred composition. The most highly preferred group of compounds are those in which (1) more than one of the R groups is of the above-indicated preferred compositions and (2) is the group

wherein
$R_3$, $R_4$ and $R_5$ are each methyl,
$R_3$, $R_4$ and $R_5$ are each ethyl or
$R_3$ and $R_4$ are each ethyl and $R_5$ is H.

The most preferred compound is 2,2-diethyl-N-(1-methyl-1-H-(1)benzothieno[3,2-c]pyrazol-3-yl)butanamide.

Synthesis

The compounds of this invention are made by the following sequence of reactions:

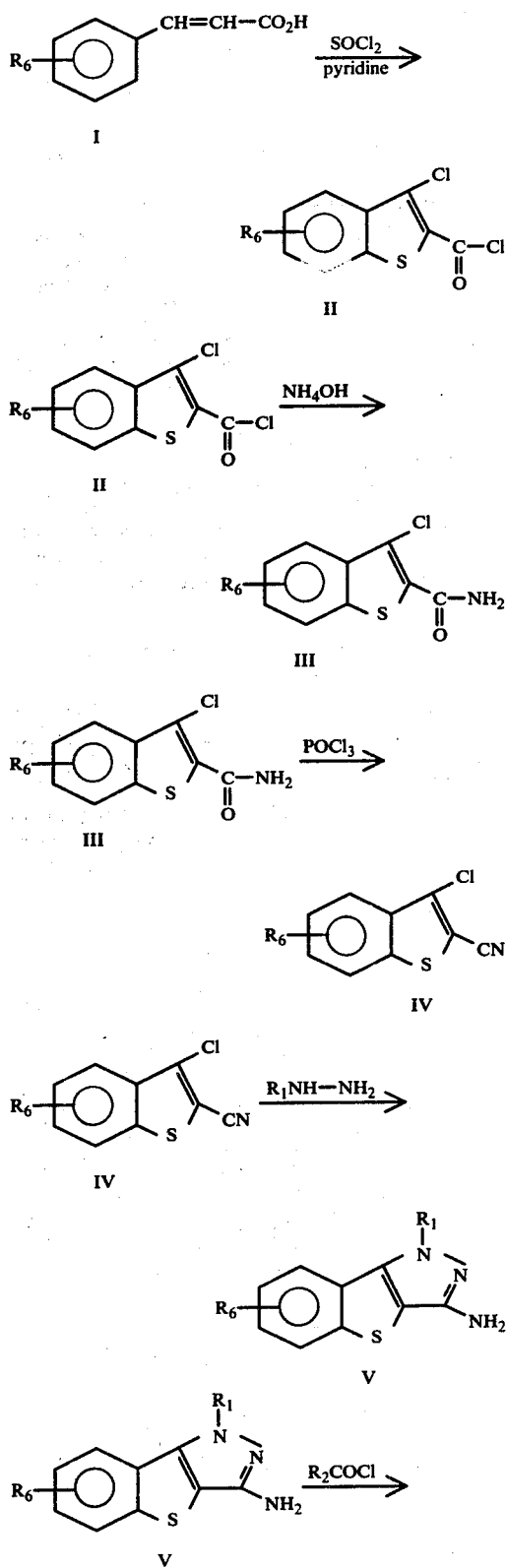

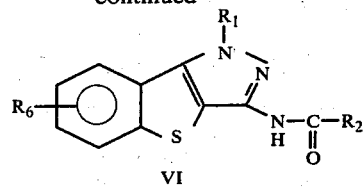

The compounds of this invention are prepared by treating a suitable cinnamic acid (I) with thionyl chloride, and pyridine in chlorobenzene [Reaction (1)] to obtain a corresponding 3-chlorobenzo[b]thiophene-2-carbonyl chloride (II). Treatment of the acid chloride in tetrahydrofuran with ammonium hydroxide [Reaction (2)] furnishes the amide (III) which is then converted to the corresponding 3-chlorobenzo[b]thiophene-2-carbonitrile (III) by refluxing in phosphorus oxychloride [Reaction (3)].

Reaction of the carbonitrile with methylhydrazine [Reaction (4)] gives the 1-methyl-1H-(1)benzothieno-[3,2-c]pyrazol-3-amine (V) which can be combined with various acid chlorides to give the desired amide.

Other compounds which are suitable as starting materials for the amide compounds of the invention include 3-chlorobenzo[b]thiophene-2-carboxamides. These have been discovered by Brabender and Wright in J. Het. Chem., 8, 711 (1971).

The following are illustrations of the N-(benzothienopyrazol)amides of the invention which can be prepared by the above sequence of reactions:

N-(1-methyl-1H-(1)benzothieno[3,2-c]pyrazol-3-yl)-acetamide

N-(1-methyl-1H-(1)benzothieno[3,2-c]pyrazol-3-yl)-heptanamide 3-chloro-N-(1-methyl-1H-(1)-benzothieno[3,2-c]pyrazol-3-yl)propanamide 3,3-dichloro-N-(1-methyl-1H-(1)benzothieno[3,2-c]-pyrazol-3-yl)-2,2-dimethylpropanamide N-(1-methyl-1H-(1)benzothieno[3,2-c]pyrazol-3-yl)cyclohexanamide N-(1-methyl-1H-(1)benzothieno[3,2-c]pyrazol-3-yl-benzamide N-(1-methyl-1H-(1)benzothieno[3,2-c]pyrazol-3-yl)-3-pyridinecarboxyamide 2-methyl-N-(5-chloro-1-methyl-1H-(1)benzothieno[3,2-c]-pyrazol-3-yl)propanamide 2-methyl-N-(6-chloro-1-methyl-1H-(1)benzothieno[3,2-c]-pyrazol-3-yl)propanamide 2-methyl-N-(8-chloro-1-methyl-1H-(1)benzothieno[3,2-c]-pyrazol-3-yl)propanamide 2-ethyl-N-(6-fluoro-1-methyl-1H-(1)benzothieno[3,2-c]-pyrazol-3-yl)butanamide N-(1,6-dimethyl-1H-(1)benzothieno[3,2-c]pyrazol-3-yl)-acetamide N-(1-ethyl-6-methyl-1H-(1)benzothieno[3,2-c]pyrazol-3-yl)acetamide The pharmaceutically acceptable salts of compounds, when $R_2$ is 3-pyridyl or $R_6$ is amine, are, of course, included within the scope of the invention. By "pharmaceutically acceptable salts" is meant salts of the above-referred compounds having a nontoxic anionic moiety such as hydrochloride, hydrobromide, sulfate, phosphate, or nitrate. Of these, the hydrochlorides are preferred.

Of the compounds of this invention, the following are preferred due to their high level of antirhinovirus activity.

2,2-dimethyl-N-(1-methyl-1H-(1)benzothieno[3,2-c]pyrazol-3-yl)propanamide 2-ethyl-N-(1-methyl-1H-(1)benzothieno[3,2-c]pyrazol-3-yl)butanamide 2,2-diethyl-N-(1-methyl-1H-(1)benzothieno[3,2-c]pyrazol-3-yl)butanamide The most preferred compound is 2,2-diethyl-N-(1-methyl-1H-(1)benzothieno[3,2-c]pyrazol-3-yl)butanamide.

The following examples illustrate the preparation of compounds of the invention.

EXAMPLE 1

N-(1-Methyl-1H-(1)benzothieno[3,2-c]pyrazol-3-yl]-propanamide

A stirred mixture of 0.2 mole of 3-chlorobenzo-[b]thiophene-2-carboxamide in 150 ml. of phosphorus oxychloride was refluxed for three hours. The reaction mixture was then cooled to room temperature and poured onto 1 kg of ice to give a solid product which was collected by filtration. Recrystallization from 1-chlorobutane gave 3-chlorobenzo[b]thiophene-2-carbonitrile, m.p. 124°–125° C.

A solution of 0.2 mole of the carbonitrile and 28.0 g. of methylhydrazine in 400 ml. of dimethyl sulfoxide was stirred and heated overnight at 80° C. The reaction mixture was cooled to room temperature and poured into 1.5 liters water to give a precipitate which was filtered and the solids thoroughly washed with water. Recrystallization from chloroform gave 1-methyl-1H-(1)benzothieno[3,2-c]pyrazol-3-amine, m.p. 177°–178° C.

A solution of 1.8 g. of propionyl chloride in 10 ml. of methylene chloride was added to a stirred solution of 0.01 mole of the above-referred amine in 50 ml. of methylene chloride containing 2.0 ml. of pyridine. The resulting clear solution was stirred overnight at room temperature and then washed with water, 5% aqueous hydrochloric acid, water, 10% aqueous sodium bicarbonate and finally with water. The upper organic layer was dried over magnesium sulfate and concentrated in vacuo to give a solid residue. This residue was recrystallized from ethanol to give N-(1-methyl-1H-(1)-benzothieno[3,2-c]pyrazol-3-yl)propanamide, m.p. 88°–89° C.

EXAMPLE 2

2-Methyl-N-(5-chloro-1-methyl-1H-(1)benzothieno[3,2-c]pyrazol-3-yl)propanamide

A stirred mixture of 0.2 mole of 3-chlorocinnamic acid in a solution containing 200 ml. of chlorobenzene, 75 ml. of thionyl chloride and 2.0 ml of pyridine was heated at reflux for 72 hours and filtered while hot to remove insoluble material. The filtrate was concentrated to remove the solvent and the solid residue was recrystallized from toluene to give 3,7-dichlorobenzo[b]thiophene-;b 2-carbonyl chloride, m.p. 100°–102° C.

A solution of 0.2 mole of the acid chloride in 500 ml. of benzene was added to a stirred mixture of 200 ml. of concentrated ammonium hydroxide and 100 ml of benzene. The solid product that formed was collected by filtration and recrystallized from ethanol to give 3,7-dichlorobenzo[b]thiophene-2-carboxamide, m.p. 225°–229° C.

By substituting this amide for the amide employed in Example 1, the corresponding 3,7-dichlorobenzo[b]thiophene-2-carbonitrile, m.p. 124°–128° C., was obtained. Treatment of this nitrile was methylhydrazine in dimethyl sulfoxide gave 5-chloro-1-methyl-1H-(1)-benzothieno[3,2-c]pyrazol-3-amine, m.p. 239°–241° C. Reaction of this amine with isobutyryl chloride followed by work up as described in Example 1 gave 2-methyl-N-(5-chloro-1-methyl-1H-(1)benzothieno[3,2-c]pyrazol-3-yl)-propanamide, m.p. 218°–219° C.

EXAMPLE 3

6,7-Dimethoxy-1-methyl-1H-(1)benzothieno[3,2-c]pyrazol-3-amine

By substituting 3,4-dimethoxycinnamic acid for the cinnamic acid employed in Example 2, the corresponding 3-chloro-5,6-dimethoxybenzo[b]thiophene-2-carbonyl chloride, m.p. 202°–204° C., was obtained. Treatment of this acid chloride with ammonium hydroxide in tetrahydrofuran gave 3-chloro-5,6-dimethoxybenzo[b]thiophene-2-carboxyamide, m.p. 173°–175° C. Treatment of the amide with phosphorus oxychloride then gave 3-chloro-5,6-dimethoxybenzo[b]thiophene-2-carbonitrile. Treatment of this nitrile with methylhydrazine in dimethyl sulfoxide gave 6,7-dimethoxy-1-methyl-1H-(1) benzothieno[3,2-c]pyrazol-3-amine, m.p. 208°–209° C.

EXAMPLES 4–6

The procedure of Example 3 was repeated, substituting the indicated "Acid" for the 3,4-dimethoxycinnamic acid of Example 3, to yield the indicated "Amine".

| Example | Acid | Amine |
| --- | --- | --- |
| 4 | 4-methylcinnamic acid | 1,6-dimethyl-1H-(1)-benzothieno[3,2-c]-pyrazol-3-amine; |
| 5 | 4-fluorocinnamic acid | 6-fluoro-1-methyl-1H-(1)-benzothieno[3,2-c]-pyrazol-3-zmine; |
| 6 | 3,4-methylenedioxy-cinnamic acid | 1-methyl-1H-[1,3]dioxolo-[4,5-f]-(1)benzothieno-[3,2-c]pyrazol-3-amine. |

EXAMPLE 7

N-(1-Methyl-1H-(1)benzothieno[3,2-c]pyrazol-3-yl)-3-pyridinecarboxamide Hydrochloride A solution of 14.2 g. of nicotinic acid chloride in 100 ml. of methylene chloride was added to a stirred solution of 0.1 mole of 1-methyl-1H-(1)benzothieno-[3,2-c]pyrazol-3-amine in 400 ml. of methylene chloride containing 10 ml. of pyridine. The reaction mixture was stirred overnight at room temperature and the precipitate which formed was collected by filtration. Recrystallization from glacial acetic acid/concentrated hydrochloric acid gave N-(1-methyl-1H-(1)benzothieno[3,2-c]pyrazol-3-yl)-3-pyridinecarboxamide hydrochloride, m.p. 298°–300° C.

EXAMPLE 8

N-(1,6-Dimethyl-1H-(1)benzothieno[3,2-c]pyrazol-3-yl)-acetamide

A solution of 0.1 mole of 1,6-dimethyl-1H-(1)-benzothieno[3,2-c]pyrazol-3-amine and 30.0 g. of acetic anhydride in 180 ml. of tetrahydrofuran was heated under reflux for 1 hour. The reaction mixture was then cooled to 20° C. and the precipitate which formed was collected by filtration. Recrystallization from N,N-dimethyl formamide/water gave N-(1,6-dimethyl-1H-(1)benzothieno-[3,2-c]pyrazol-3-yl)acetamide, m.p. 253°–255° C.

EXAMPLE 9

N-(6,7-Dihydroxy-1-methyl-1H-(1)benzothieno[3,2-c]-pyrazol-3-yl)acetamide, Diacetate A solution of 0.1 mole of 6,7-dimethoxy-1-methyl-1H-(1)benzothieno[3,2-c]pyrazol-3-amine in 300 ml. of 48% aqueous hydrobromic acid was refluxed for 3 hours. The warm reaction mixture was poured into 1 liter of water and the aqueous mixture was adjusted to pH 7 using concentrated ammonium hydroxide solution. The precipitate which formed was removed by filtration and recrystallized from N,N-dimethyl formamide/water to give 6,7-dihydroxy-1-methyl-1H-(1)benzothieno[3,2-c]pyrazol-3-amine, m.p. 305°–307° C.

A solution of 0.1 mole of the amine, 30.0 g. of acetic anhydride and 30.0 g. of pyridine in 250 ml. of tetrahydrofuran was heated under reflux for 1 hour. The warm reaction mixture was poured into 1 liter of water to give a crystalline product which was collected by filtration. Recrystallization from N,N-dimethyl-formamide/water yielded N-(6,7-dihydroxy-1-methyl-1H-(1)-benzothieno[3,2-c]pyrazol-3-yl)acetamide, diacetate, m.p. 246°–247° C.

EXAMPLE 10

2-Ethyl-N-(6-amino-1-methyl-1H-(1)benzothieno-[3,2-c]pyrazol-3-)propanamide

By substituting 3-chloro-6-nitrobenzo[b]thiophene-2-carboxamide for the amide employed in Example 1, the corresponding 3-chloro-6-nitrobenzo[b]thiophene-2-carbonitrile, m.p. 204°–205° C., was obtained.

A stirred suspension of 0.1 mole of the nitrile in a mixture of 200 ml. of concentrated hydrochloric acid and 200 ml. of glacial acetic acid containing 72.0 g. of stannous chloride was heated to a temperature of 90° C. At this temperature heating was stopped and the reaction mixture was allowed to cool to room temperature. The product which separated was dissolved in 5% hydrochloric acid solution and filtered to remove any insoluble material. The filtrate was made basic with concentrated ammonium hydroxide solution and the precipitated solid was taken up in methylene chloride. After drying over potassium carbonate, the methylene chloride was removed in vacuo to give a solid residue. Recrystallization of this residue from nitromethane gave 6-amino-3-chlorobenzo-[b]thiophene-2-carbonitrile, m.p. 158°–160° C.

A solution of 19.0 g. of benzyl chloroformate in 100 ml. of methylene chloride was added to a stirred solution of 0.1 mole of the amine in 500 ml. of methylene chloride containing 20 ml. of pyridine. The reaction mixture was stirred overnight at room temperature and then concentrated to dryness in vacuo. The solid residue was triturated with 5% hydrochloric acid solution and then recrystallized from ethanol to yield 6-carbobenzyloxyamino-3-chlorobenzo[b]thiophene-2-carbonitrile, m.p. 155°–166° C.

Treatment of this nitrile with methylhydrazine in dimethyl sulfoxide gave 6-carbobenzyloxyamino-1-methyl-1H-(1)benzothieno[3,2-c]pyrazol-3amine, m.p. 184° C. Reaction of 0.1 mole of this amine with 2-ethylbutyryl chloride, followed by work up as described in Example 1 gave 2-ethyl-N-(6-carbobenzyloxyamino-1-methyl-1H-(1) benzothieno[3,2-c]pyrazol-3-yl)propanamide.

A suspension of this crude amide in 200 ml of 48% hydrobromic acid in acetic acid was stirred at room temperature for several hours until it was all dissolved. The reaction mixture was then diluted with ether and the solid precipitate that formed was collected by filtration. The solid was distributed between methylene chloride and 10% sodium bicarbonate solution and the organic layer was separated and dried over potassium carbonate. The residue obtained after removal of the solvent in vacuo was chromatographed on silica gel, using toluene/ethyl acetate as solvents, to yield a crystalline product. Recrystallization of this product from nitromethane gave 2-ethyl-N-(6-amino-1-methyl-1H-(1)benzothieno[3,2-c]-pyrazol-3-yl)propanamide, m.p. 196°–197° C.

EXAMPLES 11–60

Employing the procedure described in Example 1, various 1-methyl-1H-(1)benzothieno[3,2-c]pyrazol-3-amines were reacted with acid chlorides to produce compounds of the subject case, for example:

| Example | R$_6$ | R$_2$ | m.p. | Formula | Found: C, H, N |
|---|---|---|---|---|---|
| 11 | H | 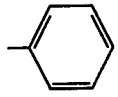 | 176–7° | C$_{17}$H$_{13}$N$_3$OS | 65.88;4.44;13.92 |
| 12 | H | —(CH$_2$)$_2$CH$_3$ | 154–6° | C$_{14}$H$_{15}$N$_3$OS | 61.68;5.42;15.23 |
| 13 | H | —(CH$_2$)$_3$CH$_3$ | 120–1° | C$_{15}$H$_{15}$N$_3$OS | 62.69;5.84;14.63 |
| 14 | H | —CH(CH$_3$)$_2$ | 200–1° | C$_{14}$H$_{15}$NOS | 59.80;4.92;15.30 |
| 15 | H | 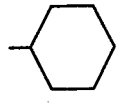 | 185–6° | C$_{17}$H$_{19}$N$_3$OS | 65.09;6.16;13.34 |
| 16 | H | —CH$_2$CH$_2$Cl | 208–9° | C$_{13}$H$_{12}$ClN$_3$OS | 53.31;4.57;14.41 |
| 17 | H | —(CH$_2$)$_4$CH$_3$ | 87–9° | C$_{16}$H$_{19}$N$_3$OS | 64.31;6.40;13.36 |
| 18 | H | —C(CH$_3$)$_3$ | 145–6° | C$_{15}$H$_{17}$N$_3$OS | 63.00;5.61;14.57 |
| 19 | 6-Cl | ${+}$CH$_2{\rightarrowtail}$CH$_3$ | 175–6° | C$_{15}$H$_{16}$ClN$_3$OS | 55.64;4.94;12.78 |
| 20 | H | —CH$_2$CH(CH$_3$)$_2$ | 149–151° | C$_{15}$H$_{17}$N$_3$OS | 62.50;5.80;14.77 |
| 21 | 6-Cl | —CH$_2$CH(CH$_3$)$_2$ | 224–4.5° | C$_{15}$H$_{16}$ClN$_3$OS | 55.74;4.86;13.29 |
| 22 | 6-Cl | —CH(CH$_3$)$_2$ | 162.5–3.5° | C$_{14}$H$_{14}$ClN$_3$OS | 54.40;4.75;13.88 |
| 23 | H | —CH$_2$C(CH$_3$)$_3$ | 174–5° | C$_{16}$H$_{19}$N$_3$OS | 63.71;6.18;13.92 |

-continued

| Example | R₆ | R₂ | m.p. | Formula | Found: C, H, N |
|---|---|---|---|---|---|
| 24 | 6-Cl | 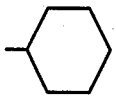 | 229–230° | $C_{15}H_{16}ClN_3OS$ | 58.74;5.47;12.02 |
| 25 | 6-Cl | —C(CH₃)₃ | 165–6° | $C_{15}H_{16}ClN_3OS$ | 56.22;5.28;12.91 |
| 26 | H | 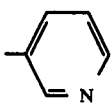 | 226–7° | $C_{16}H_{12}N_4OS$ | 62.10;3.85;18.04 |
| 27 | H | 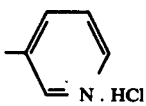 | 298–300.5° | $C_{16}H_{12}N_4OS \cdot HCl$ | 55.89;3.84;16.06 |
| 28 | H | —(CH₂)₄Cl | 167.5–9° | $C_{15}H_{16}ClN_3OS$ | 56.16;5.00,12.79 |
| 29 | H | —(CH₂)₃Cl | 211–12° | $C_{14}H_{14}ClN_3OS$ | 54.26;4.66;13.52 |
| 30 | H | —C(CH₃)₂(CH₂)₂CH₃ | 120–2° | $C_{17}H_{21}N_3OS$ | 64.42;6.74;13.33 |
| 31 | H | —CH(CH₃)(CH₂)₂CH₃ | 140–1° | $C_{16}H_{19}N_3OS$ | 63.75;6.35;13.71 |
| 32 | 5-Cl | —C(CH₃)₃ | 199–201° | $C_{15}H_{16}ClN_3OS$ | 56.14;5.17;12.98 |
| 33 | H | —C(CH₂CH₃)₃ | 155–7° | $C_{18}H_{23}N_3OS$ | 65.36;6.91;12.57 |
| 34 | H | —CH(CH₂CH₃)₂ | 168–9° | $C_{16}H_{19}N_3OS$ | 63.65;6.25;13.55 |
| 35 | H | —(CH₂)₂CH(CH₃)₂ | 124.5–5° | $C_{16}H_{18}N_3OS$ | 63.54;6.24;13.67 |
| 36 | H | —CH(CH₃)CH₂CH₃ | 146.5–7.5° | $C_{15}H_{17}N_3OS$ | 62.44;6.18;14.25 |
| 37 | 6-Cl | —(CH₂)₂CH₃ | 150–1° | $C_{14}H_{14}ClN_3OS$ | 54.48;4.58;13.70 |
| 38 | 5-Cl | —CH(CH₃)₂ | 218–219° | $C_{14}H_{14}ClN_3OS$ | 55.07;4.80;13.71 |
| 39 | 8-Cl | —CH(CH₃)₂ | 196.5–197° | $C_{14}H_{14}ClN_3OS$ | 54.90;4.70;13.35 |
| 40 | 6-F | 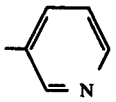 | 238–9° | $C_{16}H_{11}FN_4OS$ | 58.79;3.58;17.34 |
| 41 | 6-F | —CH(CH₂CH₃)₂ | 179.5–181° | $C_{16}H_{18}FN_3OS$ | 60.3;5.65;13.38 |
| 42 | 6-F | 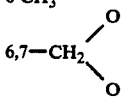 | 309–313° dec. | $C_{16}H_{11}FN_4OS \cdot HCl \cdot \tfrac{1}{4}H_2O$ | 51.88;3.62;15. |
| 43 | H | —(CH₂)₅CH₃ | 90–1° | $C_{17}H_{21}N_3OS$ | |
| 44 | 6-CH₃ | —CH₃ | 253–255° C. | | |
| 45 | 6-CH₃ | —CH(CH₃)₂ | 175–177° C. | | |
| 46 | 6-CH₃ | —CH₂—CH(CH₃)₂ | 191–193° C. | | |
| 47 | 6-CH₃ | —(CH₂)₃CH₃ | 144–145° C. | | |
| 48 | 6-CH₃ | —C(CH₃)₃ | 136–138° C. | | |
| 49 | 6,7—OCH₂O— | —C(CH₃)₃ | 250–251° C. | | |
| 50 | 6,7—OCH₂O— (see struct) | —CH(CH₃)₂ | 244–246° C. | | |
| 51 | 6,7—OCH₂O— (see struct) | —CH₂—CH(CH₃)₂ | 223–224° C. | | |
| 52 | 6,7—OCH₃, —OCH₃ | —CH₃ | 218–220° C. | | |
| 53 | 6,7—OCH₃, —OCH₃ | —CH₃ | 192–193° C. | | |
| 54 | 6,7—OCH₃, —OCH₃ | —C(CH₃)₃ | 172–173° C. | | |
| 55 | 6,7—OCH₃, —OCH₃ | —C(CH₂CH₃)₃ | 216–218° C. | | |
| 56 | 6,7—OCOCH₃, —OCOCH₃ | —CH₃ | 246–247° C. | | |

-continued

| Example | $R_6$ | $R_2$ | m.p. | Formula | Found: C, H, N |
|---|---|---|---|---|---|
| 57 | H | $-\underset{\underset{CH_3}{\mid}}{\overset{\overset{CH_3}{\mid}}{C}}-CHCl$ | 216–218° C. | | |
| 58 | H | $-CH_3$ | 265–266° C. | | |
| 59 | H | $-CH_2CH_3$ | 88–89° C. | | |
| 60 | 6-$NH_2$ | $-CH(CH_2CH_3)_2$ | 196–197° C. | | |
| 61 | 6-$N(CH_3)_2$ | $-CH(CH_2CH_3)_2$ | 179–180° | | |
| 62 | 6-$N(CH_2CH_3)_2$ | $-CH_3$ | | | |
| 63 | H | $-CH_2CF_3$ | | | |

Antiviral Testing

No pharmaceutical agents have been commercially available for the treatment of rhinoviral infection in man (common cold) except for symptomatic treatment. The prevention of colds with biologicals, such as vaccines, is not practical due to the large number of rhinovirus strains which cause colds, at present numbering over 100 different antigenic types. However, the compounds of this invention have been demonstrated in vitro to be broadly active. In fact, no strain has yet been shown to be resistant. Table 1 below contains a list of strains of rhinovirus which have been tested and found to be inhibited by the compounds of this invention.

TABLE I

RHINOVIRUS TYPES TESTED AND INHIBITED BY N-(benzothienopyrazol)amides

| Type | Strain |
|---|---|
| 1A | 2060 |
| 1B | B632 |
| 2 | HGP |
| 3 | FEB |
| 5 | Norman |
| 13 | 353 |
| 14 | 1059 |
| 15 | 1734 |
| 39 | 209 |
| 41 | 56110 |
| 51 | F01-4081 |
| Not yet typed | 998 |
| " | 1426 |
| " | 1492 |
| " | 1662 |
| " | 4006 |
| " | 6579 | concentrations is between 0.1 mg/ml and 20 mg/ml, with a preferred range between 0.1 and 2.0 mg/ml.

Test Procedures

To those skilled in the art, the following procedure will be recognized as similar to the protocol of Fiala[2], an established method in the field of virology.

[2]Fiala, M., "Plaque Formation by 55 Rhinovirus Sero Types," Applied Microbiology, 16, 1445 (1968).

Rhinovirus-sensitive HeLa cells are grown to confluent monolayers and infected with approximately 100 rhinovirus particles and subsequently covered with an agar-containing medium having varying concentrations of the test chemical. After 3 to 4 days of incubation at 34° C., the agar is removed and the plates stained with crystal violet. The amount of inhibition is determined by the reduction in the number of plaques in the cell layer, the minimum inhibitory composition (MIC) being that concentration of compound required to completely suppress plaque formation.

Using the above procedure, some of the compounds which constitute the preferred embodiment of the present invention are exemplified below, with appropriate minimum inhibitory concentrations given for each experiment.

EXAMPLE 61

2,2-Diethyl-N-(1-methyl-1H-(1)benzothieno-[3,2-c]pyrazol-3-yl)butanamide was suspended in distilled water at 100 μg/ml and sufficient amounts added to an overlay to provide concentrations of 0.1 μg/ml to 2.0 μg/ml. The following results were obtained:

| Treatment | Concentration (μg/ml) | 1A | 3 | 14 | Rhinovirus Types 15 | 39 | 51 | 998 | 1492 |
|---|---|---|---|---|---|---|---|---|---|
| | | | | | (Plaque counts per plate) | | | | |
| None | 0 | 211 | 170 | 194 | 145 | 112 | 118 | 190 | 255 |
| Compound at | 0.1 | 153 | 119 | 125 | 61 | 65 | 211 | 103 | 140 |
| Compound at | 0.5 | 60 | 0 | 20 | 0 | 4 | 28 | 0 | 12 |
| Compound at | 1.0 | 4 | 0 | 0 | 0 | 0 | 0 | 0 | 0 |
| Compound at | 2.0 | 0 | 0 | 0 | 0 | 0 | 0 | 0 | 0 |
| MIC in μg/ml | | 2.0 | 0.5 | 1.0 | 0.5 | 1.0 | 1.0 | 0.5 | 1.0 |

Treatment, using formulations well known to the skilled pharmaceutical chemist, may be oral or intranasal; however, oral treatment is the preferred method. An oral dose range, using tablets or capsules, of 2 to 50 mg/kg/dose with doses given as frequently as every 4 hours or as little as once a day, is the suggested regimen of dosing. Pharmaceutical preparations of sustained release compositions can also be used as oral dosage forms.

In using the intranasal route, effective methods include administration by intranasal drops, by nebulizer, or aerosol of useful droplet size. An acceptable range of It can be seen that complete suppression of virus growth, i.e., inhibition of plaque formation, was observed at the minimum inhibitory concentration (MIC). These data demonstrate the anti-rhinoviral activity of subject compound against eight strains of rhinovirus.

EXAMPLES 62–66

Using methodology similar to Example 61, several additional compounds were tested. The results are shown in Table 3. These compounds all exhibited potent antiviral activity.

|  | CH₃ |
|--|--|
|  | (structure shown) |

| Antiviral Spectrum | Minimium Inhibitor Concentrations (μg/ml) Example Numbers | | | | |
|---|---|---|---|---|---|
| Rhinovirus Types | 62[1] | 63[2] | 64[3] | 65[4] | 66[5] |
| 1a | 6 | 1 | 1 | 8 | 5 |
| 1b | 2 | 2 | 2 | 6 | 2 |
| 2 | 2 | 2 | 2 | 4 | 2 |
| 3 | 4 | 0.5 | 1 | 4 | 6 |
| 5 | 2 | 2 | 2 | 4 | 2 |
| 13 | 2 | 2 | 2 | 5 | 2 |
| 14 | 6 | 1 | 1 | 8 | 8 |
| 15 | 5 | 0.5 | 1 | 5 | 4 |
| 39 | 2 | 0.5 | 1 | 8 | 2 |
| 41 | 2 | 2 | 2 | 2 | 2 |
| 51 | 8 | 1.0 | 2 | 8 | 6 |
| 998 | 2 | 1 | 1 | 8 | 2 |
| 1425 | 2 | 2 | 4 | 2 | 2 |
| 1492 | 2 | 1 | 2 | 8 | 6 |
| 1662 | 8 | 1 | 2 | 10 | 8 |
| 4005 | 2 | 2 | 2 | 2 | 2 |
| 6579 | 2 | 2 | 2 | 5 | 2 |

[1] In Example 62, R = —COCH₂—(cyclopentyl)
[2] In Example 63, R = —COCH(C₂H₅)CH₂CH₃
[3] In Example 64, R = —COCH₂CH(CH₃)₂
[4] In Example 65, R = —COCH₃
[5] In Example 66, R = —CO—(3-pyridyl) · HCl The compounds of this invention may be employed in useful pharmaceutical compositions such as oral dosage forms, e.g. tablets, hard gelatin capsules, soft gelatin capsules and aqueous suspensions, and intranasal drops.

Used orally, the compounds of this invention will have a therapeutic dose range in humans from 2.0 to 300 mg/kg/day. The dosage forms described below are designed to deliver this therapeutic dose.

EXAMPLE 67

Hard gelatin capsules can be prepared by filling standard two-piece hard gelatin capsules with the following mixture using conventional encapsulating equipment:
Active Ingredient 200 mg.
Lactose 225 mg.
Talc 25 mg.
Magnesium Stearate 8 mg.

EXAMPLE 68

The following mixture is prepared and injected in gelatin by means of a positive displacement pump to from soft gelatin capsules; the capsules are washed in petroleum ether and dried.
Active Ingredient 200 mg.
Polysorbate 80 150 mg.
Glycerin 15 mg.
Purified Water 8 mg.

EXAMPLE 69

Tablets can be prepared by conventional procedures so that each tablet will contain:
Active Ingredient 200 mg.
Spray Dried Lactose 300 mg.
Microcrystalline 30 mg. Cellulose
Polyvinylpyrrolidone 3 mg.
Magnesium Stearate 4 mg.

EXAMPLE 70

An aqueous suspension for oral administration is prepared so that each 5 ml. contains:
Active Ingredient 200 mg.
Carboxy methyl cellulose 5%
Syrup 35%
Glycerin 10%
Sorbitol 10%
Methyl Cellulose 5%
Sodium Benzoate 5 mg.
Flavor .1%
Water Q.S. 5 cc.

In practicing the intranasal route, effective methods include administration by intranasal drops, by nebulizer or aerosol. An acceptable range of concentrations is between 0.1 mg/ml and 20 mg/ml, with a preferred range between 1.0 and 2.0 mg/ml. The following examples are designed to deliver this effective dose.

EXAMPLE 71

| Intranasal Drops | |
|---|---|
| Active Ingredient | 1.0 mg/ml |
| Surfactant | 0.05 mg/ml |
| Propylene Glycol 50 | qs 1 ml |
| Ethanol 50 | |

EXAMPLE 72

| Nebulizer | |
|---|---|
| Active Ingredient | 1.0 mg/ml |
| Surfactant | 0.05 mg/ml |
| Ethanol 10 | qs 1 ml |
| Water 90 | |

EXAMPLE 73

| Aerosol | |
|---|---|
| Active Ingredient | 1.0 mg/ml |
| Surfactant | 0.05 mg/ml |
| Ethanol 10/ | |
| Water 40/ | |
| Propellant 50 | qs 1 ml |

It will be recognized by those skilled in the art that a wide variety of other pharmaceutical carriers, diluents, and additives can be used. These are described in "Remington's Pharmaceutical Sciences" by E. W. Martin, a well-known reference in this field.

What is claimed is:

1. A compound of the formula

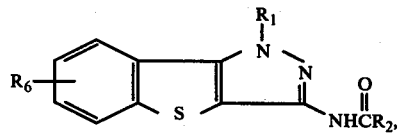

wherein
R₁ is methyl or ethyl;
R₂ is selected from cyclohexyl, phenyl, 3-pyridyl, C₂₋₅ haloalkyl having 1-3 halogen substituents in other than the α-position with respect to the carbonyl group, C$_{2-5}$ alkoxyalkyl having the alkoxy moiety in other than the α-position with respect to the carbonyl group, and the group

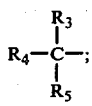

wherein
R$_3$ and R$_4$ are independently selected from H, methyl, and ethyl;
R$_5$ is selected from H and C$_{1-5}$ alkyl;
R$_6$ is H, Cl, F, methyl, 6,7-methylenedioxy, 6,7-dimethoxy, 6,7-diacetoxy or the amine group —NR$_7$R$_8$, wherein R$_7$ and R$_8$ are independently selected from H, methyl and ethyl;
and, when R$_2$ is 3-pyridyl or R$_6$ is amine, pharmaceutically suitable acid addition salts thereof, provided that
(a) when R$_2$ is cyclohexyl, R$_6$ is H or methyl;
(b) when R$_2$ is phenyl, R$_6$ is H; and
(c) when R$_2$ is 3-pyridyl, R$_6$ is H or F.

2. A compound of claim 1 in which R$_1$ is methyl.
3. A compound of claim 1 in which R$_2$ is 3-pyridyl.
4. A compound of claim 1 in which R$_2$ is chloroalkyl.
5. A compound of claim 1 in which R$_2$ is

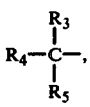

wherein
R$_3$ and R$_4$ are independently methyl or ethyl, and R$_5$ is H, methyl or ethyl.

6. A compound of claim 1 in which R$_6$ is H.
7. A compound of claim 5 in which R$_3$, R$_4$ and R$_5$ are methyl.
8. A compound of claim 5 in which R$_3$, R$_4$ and R$_5$ are ethyl.
9. A compound of claim 5 in which R$_3$ and R$_4$ are ethyl and R$_5$ is H.
10. The compound 2,2-diethyl-N-(1-methyl-1H-(1)-benzothieno[3,2-c]pyrazol-3-yl)butanamide.
11. A pharmaceutical composition comprising a pharmaceutically suitable carrier and a compound of claim 1 in an amount sufficient for the prophylaxis and therapy of rhinovirus infection.
12. A pharmaceutical composition comprising a pharmaceutically suitable carrier and a compound of claim 2 in an amount sufficient for the prophylaxis and therapy of rhinovirus infection.
13. A pharmaceutical composition comprising a pharmaceutically suitable carrier and a compound of claim 3 in an amount sufficient for the prophylaxis and therapy of rhinovirus infection.
14. A pharmaceutical composition comprising a pharmaceutically suitable carrier and a compound of claim 4 in an amount sufficient for the prophylaxis and therapy of rhinovirus infection.
15. A pharmaceutical composition comprising a pharmaceutically suitable carrier and a compound of claim 5 in an amount sufficient for the prophylaxis and therapy of rhinovirus infection.
16. A pharmaceutical composition comprising a pharmaceutically suitable carrier and a compound of claim 6 in an amount sufficient for the prophylaxis and therapy of rhinovirus infection.
17. A pharmaceutical composition comprising a pharmaceutically suitable carrier and a compound of claim 7 in an amount sufficient for the prophylaxis and therapy of rhinovirus infection.
18. A pharmaceutical composition comprising a pharmaceutically suitable carrier and a compound of claim 8 in an amount sufficient for the prophylaxis and therapy of rhinovirus infection.
19. A pharmaceutical composition comprising a pharmaceutically suitable carrier and a compound of claim 9 in an amount sufficient for the prophylaxis and therapy of rhinovirus infection.
20. A pharmaceutical composition comprising a pharmaceutically suitable carrier and the compound of claim 10 in an amount sufficient for the prophylaxis and therapy of rhinovirus infection.
21. A method for the prophylaxis and therapy of rhinovirus infection in humans comprising administering thereto an effective amount of a compound of claim 1.
22. A method for the prophylaxis and therapy of rhinovirus infection in humans comprising administering thereto an effective amount of a compound of claim 2.
23. A method for the prophylaxis and therapy of rhinovirus infection in humans comprising administering thereto an effective amount of a compound of claim 3.
24. A method for the prophylaxis and therapy of rhinovirus infection in humans comprising administering thereto an effective amount of a compound of claim 4.
25. A method for the prophylaxis and therapy of rhinovirus infection in humans comprising administering thereto an effective amount of a compound of claim 5.
26. A method for the prophylaxis and therapy of rhinovirus infection in humans comprising administering thereto an effective amount of a compound of claim 6.
27. A method for the prophylaxis and therapy of rhinovirus infection in humans comprising administering thereto an effective amount of a compound of claim 7.
28. A method for the prophylaxis and therapy of rhinovirus infection in humans comprising administering thereto an effective amount of a compound of claim 8.
29. A method for the prophylaxis and therapy of rhinovirus infection in humans comprising administering thereto an effective amount of a compound of claim 9.
30. A method for the prophylaxis and therapy of rhinovirus infection in humans comprising administering thereto an effective amount of the compound of claim 10.

* * * * *